United States Patent [19]

Nagase et al.

[11] Patent Number: 5,332,818
[45] Date of Patent: Jul. 26, 1994

[54] IMMUNOSUPPRESSIVE AGENT AND PROCESS OF PRODUCING THE SAME

[75] Inventors: Hiroshi Nagase; Koji Kawai; Shu Matsumoto, all of Kamakura; Takashi Endoh, Chigasaki; Yoshiaki Katsura, Otsu; Kohei Arakawa, Kyoto, all of Japan

[73] Assignee: Toray Industries, Inc., Japan

[21] Appl. No.: 34,669

[22] Filed: Mar. 22, 1993

Related U.S. Application Data

[63] Continuation of Ser. No. 721,639, filed as PCT/JP90/01541. Nov. 28, 1990, abandoned.

[30] Foreign Application Priority Data

Nov. 28, 1989 [JP] Japan ................... 1-308491
Dec. 11, 1989 [JP] Japan ................... 1-322160
Dec. 15, 1989 [JP] Japan ................... 1-326941

[51] Int. Cl.$^5$ ........................... C07D 721/72
[52] U.S. Cl. ......................................... 546/37
[58] Field of Search ............................. 546/37

[56] References Cited

U.S. PATENT DOCUMENTS 4,443,605 4/1984 Kotick et al. ................... 546/37
4,857,533 8/1989 Sherman et al. ................. 514/282

FOREIGN PATENT DOCUMENTS 8900995 2/1989 PCT Int'l Appl.

OTHER PUBLICATIONS

Chemical Abstract vol. 108, #143295j 1988, Sultano et al, "Naltrindole, a highly selective and potent nonpeptide δ opioid receptor antagonist".
Science, pp. 62–72 (Jan. 1989).
Plotnikoff et al, Introduction: Ying–Yang Hypothesis of Immunomodulation, pp. 1–2. (1984).
Journal of Medicinal Chemistry, vol. 31, No. 2, pp. 281–282.
Carr et al., Life Sciences 47:1059 (1990).
P. S. Portoghese et al., Eur. J. Pharmacology 146:185 (1988).
Merck Index, 11th ed. pp. 6274–6274.

*Primary Examiner*—C. Warren Ivy
*Assistant Examiner*—Raymond Covington
*Attorney, Agent, or Firm*—Birch, Stewart, Kolasch & Birch

[57] ABSTRACT

An immunosuppressive agent which has low toxicity and which exhibits excellent effectiveness even if it is orally administered is presented. The immunosuppressive agent of the present invention is characterized in that it contains δ-opioid antagonist having high selectivity to δ-opioid receptor. The present invention also provides a process of producing a naltrindole derivative characterized by reacting naltrexone or a salt thereof with a phenylhydrazine derivative in a solvent in the presence of methanesulfonic acid.

10 Claims, 2 Drawing Sheets

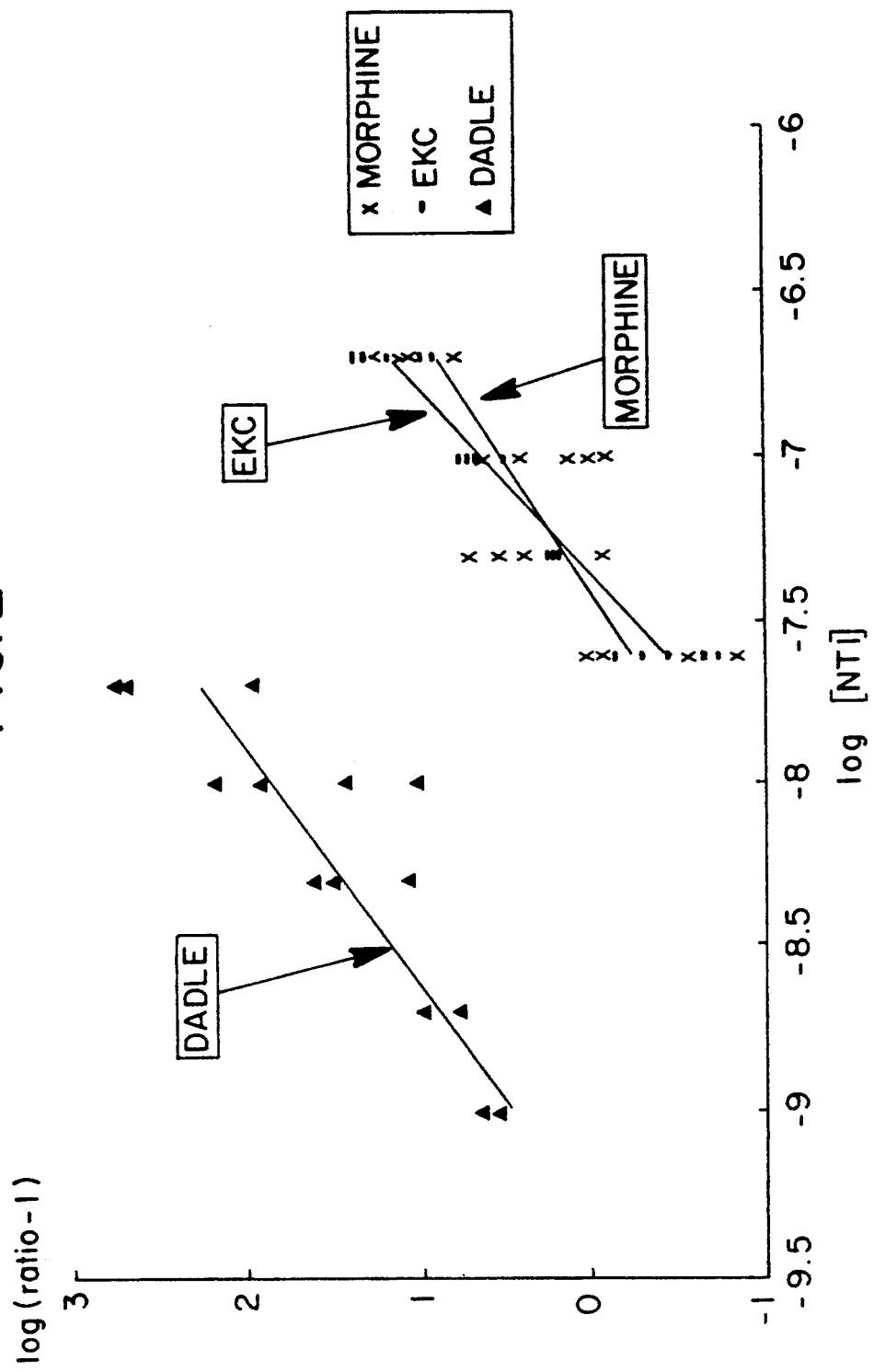

IMMUNOSUPPRESSIVE AGENT AND PROCESS OF PRODUCING THE SAME

This application is a continuation of application Ser. No. 07/721,639 filed as PCT/JP90/01541, Nov. 28, 1990, now abandoned.

TECHNICAL FIELD

The present invention relates to an immunosuppressive agent and to a process of producing the same.

BACKGROUND ART

Immunosuppressive agents are indispensable to inhibit rejection reaction mainly encountered in organ transplantations. Before 1980, no agent was known which can be called a real immunosuppressive agent. Therefore, even in the transplantation of pancreas which is thought to be the easiest one, the rate of success was only 7%. In 1980, cyclosporine A was discovered and the rate of success of organ transplantations was drastically promoted and the era of real organ transplantations initiated. However, cyclosporine A has a very strong toxicity to kidney, so that it is now tried to reduce the amount of cyclosporine A to be used as small as possible by co-employing other drugs. In 1984, FK-506 was discovered from a ray fungus. It was said that this compound has an immunosuppressive effect as high as 10 to 100 times higher than that of cyclosporine A, and at first, side effects such as toxicity to kidney are small (Science, January, 62, 1989). Recently, however, it was confirmed that FK-506 has stronger toxicity to kidney than cyclosporine A and also has a strong toxicity to liver. Thus, an effective immunosuppressive agent with low toxicity, which replaces these compounds is demanded.

In general, among the administration routes of drugs, oral administration is best preferred because it can be carried out in the absence of a doctor and patients can take the drug at their homes. However, the effectiveness of cyclosporine A when orally administered is insufficient.

On the other hand, through studies of action mechanism of analgesics such as morphine, it was found that there are sites called opioid receptors in various organs such as brain, to which these substances are specifically bound. The compounds which are bound to the receptors and exhibit pharmacological effects such as analgesic effect are called agonists.

The compounds which have affinities to the above-mentioned opioid receptors but do not exhibits opioid activities, which exhibit antagonistic effects to opioid compounds are called opioid antagonists. Known opioid antagonists, such as naloxone and naltrexone, are used for studies of analgesic effects of the agonists such as morphine, and for treatment of respiration inhibition which is a side effect caused by administration of opiates such as morphine.

It was recently found that there are three subtypes called $\mu$, $\kappa$ and $\delta$ in opioid receptors. To study each of the subtypes, ligands, that is, agonists and antagonists which are specifically bound to eachsubtype are sought. It was recently confirmed that among these subtypes, the one which causes critical addiction and inhibition of respiration which are included in the side effects of morphine is the $\mu$ receptors. It was thus suggested by this study that for synthesizing an ideal analgesic free from addiction and inhibition respiration, compounds which have high selectivity to $\mu$ receptors should be avoided and compounds which have high selectivity to $\kappa$ or $\delta$ receptors should be sought. Thus, an antagonist having high selectivity to a particular subtype of opioid receptors is necessary not only for the studies of action mechanism of analgesics but also for the development of an ideal analgesic.

It was recently found that opioid receptors concern immune system. More particularly, it was found that the agonists represented by morphine, which act on $\mu$ receptors exhibit immunosuppressive effect and agonists represented by enkephalin, which act on $\delta$ receptors exhibit immunostimulating effect (Plotnikoff, Enkephalins and Endorphins, stress and immune system, Plenum Press, 1986).

Although a number of reports have been issued concerning the immunosuppressive effects of agonists of $\mu$ receptors, which are represented by morphine, since the agonists of $\mu$ receptors exhibit critical side effects such as addiction and inhibition of respiration, it is difficult to develop an immunosuppressive agent by employing an agonist of a $\mu$ receptor.

DISCLOSURE OF THE INVENTION

An object of the present invention is to provide a novel and ideal immunosuppressive agent which has low toxicity and which exhibits sufficient immunosuppressive activity even if it is administered orally.

Another object of the present invention is to provide a process of producing the immunosuppressive agent of the present invention by which the immunosuppressive agent may be produced in a high yield without a complex work up procedure.

For attaining the above-mentioned objects, the present inventors intensively studied to discover an immunosuppressive agent which has a completely different action mechanism from those of cyclosporine A and FK-506, and a process of producing the immunosuppressive agent in a high yield, thereby completing the present invention.

That is, the present invention provides an immunosuppressive agent comprising as an effective ingredient a $\delta$-opioid antagonist or a pharmaceutically acceptable salt thereof.

The present invention also provides a process of producing a naltrindole derivative represented by the formula [6]:

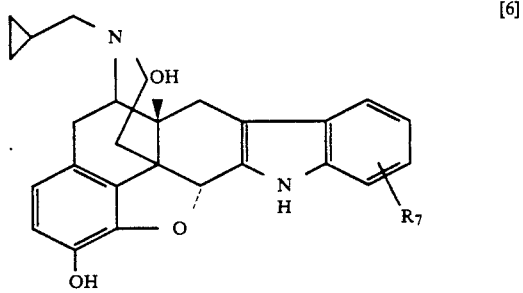

[6]

(wherein $R_7$ represents hydrogen, chlorine, bromine, fluorine, methyl, methoxy or nitro) comprising reacting naltrexone or a salt thereof with a phenylhydrazine derivative in a solvent in the presence of methanesulfonic acid.

The immunosuppressive agent of the present invention largely improves the toxicity which is the drawback of the conventional cyclosporine A and FK-506, and exhibits high immunosuppressive activity when administered not only parenterally but also orally.

By the process of producing the immunosuppressive agent according to the present invention, production of the immunosuppressive agent in a high yield by simple operation was attained.

BRIEF DESCRIPTION OF THE DRAWINGS

FIG. 2 shows antagonism of naltrindole (NTI) under varying concentrations.

BEST MODE FOR CARRYING OUT THE INVENTION

Figure 1:
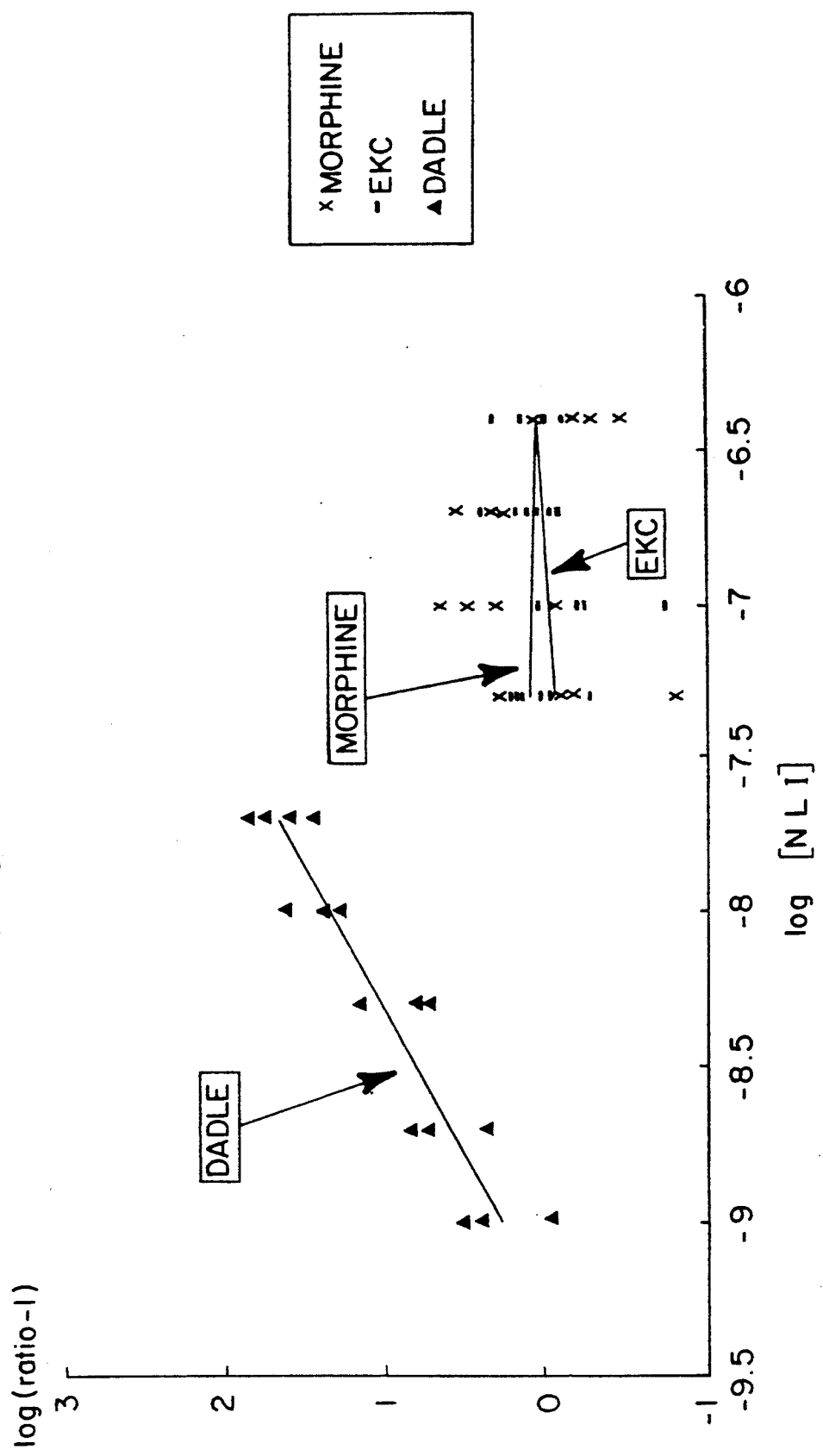
FIG. 1 shows antagonism of naloxyindole (NLI) which is an immunosuppressive agent according to the present invention under varying concentrations.

As mentioned above, the immunosuppressive agent of the present invention contains as an effective ingredient a δ-opioid antagonist or a pharmaceutically acceptable salt thereof.

The term "δ-opioid antagonist" herein used-means a group of compounds which suppress the inhibition by DADLE or DPDPE of contraction of MVD specimen caused by electric stimulation. The δ-opioid antagonist is preferably a compound having an inhibitory effect just mentioned above of not more than 50 in terms of Ke value (H. W. Kostertitz et al, Br. J. Pharmacol. Vol. 46, 764, 1972, P. S. Portoghese et al., Eur. J. Pharmacol., vol. 146, 185, 1988 ).

The Ke value is defined by the equation:

$$Ke = [antagonist]/(IC_{50} \text{ ratio} - 1)$$

The IC$_{50}$ ratio used herein is the value obtained by dividing the IC$_{50}$ of an agonist, which is measured in the presence of an antagonist, with the IC$_{50}$ value of the antagonist, that is measured in the absence of the antagonist. Ke value is a value which is introduced for compensating the concentration of antagonist when comparing the IC$_{50}$ ratio. Thus, the smaller the Ke value, the stronger the antagonist activity.

Preferred δ-opioid antagonists include those represented by the following formula [1]:

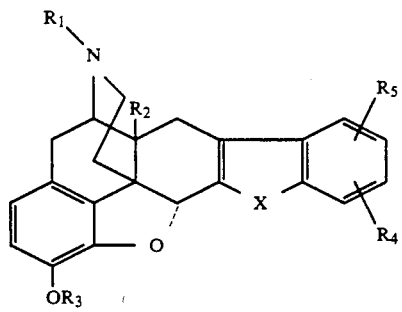

[1]

Among the compounds represented by the formula [1], especially preferred are those wherein R$_1$ is C$_1$-C$_5$ alkyl, C$_3$-C$_6$ cycloalkylalkyl, C$_5$-C$_7$ cycloalkenylalkyl, C$_7$-C$_{10}$ aralkyl, C$_4$-C$_5$ transalkenyl, allyl or furan-2-ylalkyl, R$_2$ is hydrogen or hydroxy, R$_3$ is hydrogen, R$_4$ is hydrogen, fluorine, methyl, methoxy or nitro, R$_5$ is hydrogen, X is oxygen or NR$_6$ (wherein R$_6$ represents hydrogen or C$_1$-C$_5$ alkyl).

Among these, especially preferred are those represented by the following formulae [3]–[5]:

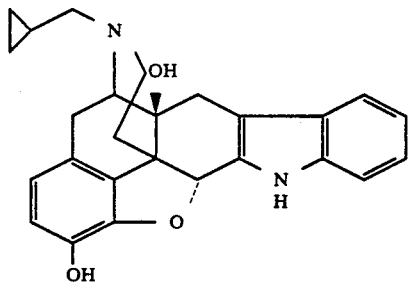

[3]

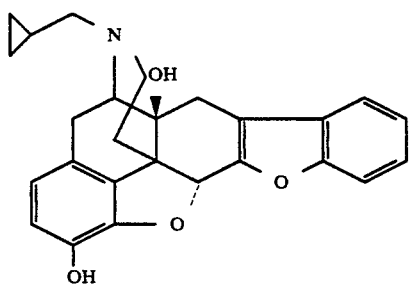

[4]

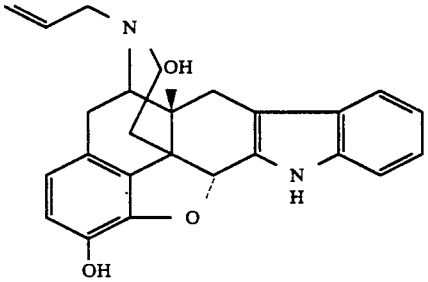

[5]

The compound of the formula [3] was named naltrindole because this compound is a ring-condensed product of naltrexone and indole (P. S. Portoghese et al., J. Med. Chem., vol. 31, No. 2, 1988), and the compound of the formula [5] was named naloxindole (NLI) similarly. The compound of the formula [4] was named naltrbenzofuran (NTB).

The compound of the following formula [2] is also a preferred δ-opioid antagonist.

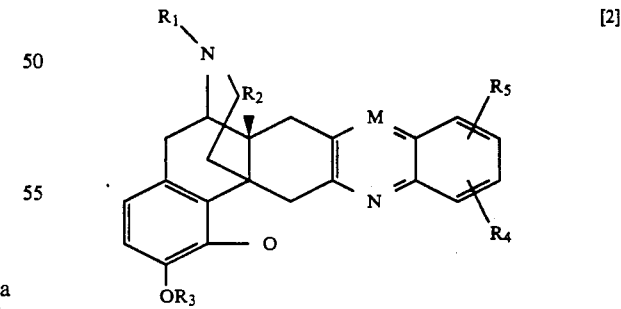

[2]

The pharmaceutically acceptable salts of the compounds represented by the formulae [1]–[5] include inorganic acid salts such as hydrochloric acid salt, sulfuric acid salt, phosphoric acid salt and the like; organic acid salts such as methanesulfonic acid salt, acetic acid salt, maleic acid salt, fumaric acid salt, benzoic acid salt, phthalic acid salt, glutaric acid salt, fumaric acid salt, succinic acid salt, citric acid salt, lactic acid salt, malic acid salt, toluene sulfonic acid salt and the like, although the salts are not restricted thereto.

The compounds represented by the formula [1] may be produced by a known process (P. S. Portoghese et al., J. Med. Chem., vol. 31, No. 2, 282, 1988 ).

Among the compounds represented by the formula [1], those wherein $R_1$ is allyl, $R_2$ is hydroxy, $R_3$ and $R_5$ are hydrogen, $R_4$ is as defined above may be obtained by the following method: That is, naloxone hydrochloride is dissolved in a solvent together with phenylhydrazine or a substituted phenylhydrazine and methanesulfonic acid is added to the mixture. After continuing the reaction under stirring, the reaction mixture is cooled to room temperature. By collecting the generated precipitate, a part of the desired product is obtained in the form of methanesulfonic acid salt. The remainder is obtained by neutralizing the mother liquor in sodium hydrogen carbonate and then extracting the resultant with a solvent. As the substituted phenylhydrazine, although not restricted thereto, phenylhydrazine substituted with halogen, methyl, methoxy or nitro, such as 2-fluorophenylhydrazine, 4-fluorophenylhydrazine, 2-methylphenylhydrazine, 4-methylphenylhydrazine, 4-methoxyphenylhydrazine, 4-nitrophenylhydrazine or the like may be employed. The hydrazine derivative may be used in the amount of 1-10 equivalents. In practice, satisfactory results may be obtained by using 1-2 equivalents of the hydrazine derivative. As the solvent, alcoholic solvents, especially ethanol, are preferred. The reaction may be carried out at a temperature of 0°-50° C., preferably 20°-90° C., most preferably about The compound of the formula [6] may be produced by treating naltrexone or a salt thereof with a phenylhydrazine derivative in a solvent in the presence of methanesulfonic acid. The compound may preferably be produced by the following process: That is, naltrexone hydrochloride or naltrexone itself is dissolved in a solvent together with a phenylhydrazine derivative and methanesulfonic acid. After continuing the reaction under stirring, the reaction mixture is cooled to room temperature. By filtration of the formed precipitates, the desired product is obtained as a pure methanesulfonic acid salt. The phenylhydrazine derivative may be used in the amount of 1-10 equivalents and satisfactory results may be obtained by using 1-2 equivalents of phenylhydrazine derivative in practice. As the solvent, alcoholic solvents, especially ethanol, are preferred. The reaction may be carried out at a temperature of 0°-150° C. preferably 20°-90° C., most preferably 75°-85° C. Methanesulfonic acid may be used in the amount of 1-20 equivalents, preferably 8-12 equivalents. As the phenylhydrazine derivative, 2-fluorophenylhydrazine, 4-fluorophenylhydrazine, 2-chlorophenylhydrazine, 4-chlorophenylhydrazine, 2-methylphenylhydrazine, 4-methylphenylhydrazine, 4-methoxyphenylhydrazine, 4-nitrophenylhydrazine and the like may be employed, although not restricted thereto.

Salts other than methanesulfonic acid salt may be obtained by suspending the generated methanesulfonic acid salt of naltrindole in an organic solvent, neutralizing the suspension with an aqueous basic solution, treating the resultant with an organic solvent so as to extract free base of naltrindole, dissolving the obtained free naltrindole in a solvent and by adding a corresponding acid.

The antagonist of the formula [2] according to the present invention may be produced by the method disclosed in International Publication No. WO89/00995.

In clinical application of the immunosuppressive agent of the present invention, the immunosuppressive agent may be formulated to an injection, capsule, suppository, oral formulation or the like. Among these, injection and oral formulation are preferably employed.

The immunosuppressive agent of the present invention may comprise the above-described δ-antagonist alone or may comprise excipients such as stabilizers, buffering agents, diluents, isotonic agents, antiseptics and the like.

The immunosuppressive agent of the present invention may preferably contain the above-described effective ingredient in the amount of 1-90% by weight, more preferably 30-70% by weight.

The dose of the immunosuppressive agent of the present invention may appropriately be selected depending on the object of administration, administration route, and conditions of the patients. The immunosuppressive agent may be administered 0.001-1 g/day in case of administration by injection and 0.01-10 g/day in case of oral administration.

The present invention will now be described by way of examples thereof. It should be noted that the present invention is not restricted by the examples.

EXAMPLE 1

Synthesis of Methanesulfonic Acid Salt and Hydrochloric Acid Salt of Naloxindole (NLI)

In 20 ml of ethanol, 1 g of naloxone hydrochloride and 0.3 ml of phenylhydrazine were dissolved and the resulting mixture was heated under reflux. To the mixture, 2.6 ml of methanesulfonic acid was added and the resulting mixture was heated under reflux with stirring for another 1.5 hours. The mixture was then cooled to room temperature and the precipitated crystals were filtered to afford 0.25 g of naloxindole methanesulfonic acid salt.

After neutralizing the mother liquor with saturated aqueous solution of sodium bicarbonate, ethanol and chloroform were added to the mixture. After stirring the resulting mixture, the mixture was filtered through Super-Cel and the filtrate was extracted with chloroform. Organic layers were combined and dried over sodium sulfate. The combined organic layers were concentrated and purified by Sephadex column (LH-20, MeOH) to give remaining naloxindole. The obtained compound was dissolved in ethyl acetate and ethyl acetate saturated with hydrochloric acid was added to the solution in icecooled water to give 0.87 g of naloxindole hydrochloride. The results of the elementary analysis of the thus obtained methanesulfonic acid salt and hydrochloric acid salt of NLI were identical with the calculated values as shown below.

Elementary Analysis of Naloxindole Methanesulfonic Acid Salt (Needle-shaped Crystals, Decomposition Point: 253°-257° C., Recrystallization Solvent: Ethanol/Chloroform); as $C_{25}H_{24}N_2O_3 \cdot MeSO_3H \cdot H_2O$

|  | C | H | N | S |
| --- | --- | --- | --- | --- |
| Calcd. | 60.68 | 5.88 | 5.44 | 6.23 |
| Found | 60.55 | 5.75 | 5.32 | 6.14 |

Elementary Analysis of NLI Hydrochloride: as $C_{25}H_{24}N_2O_3 \cdot 0.5H_2O \cdot HCl$

| | C | H | N | Cl |
|---|---|---|---|---|
| Calcd. | 67.33 | 5.88 | 6.28 | 7.95 |
| Found | 67.00 | 5.92 | 6.02 | 7.60 |

EXAMPLE 2

Synthesis of Naloxindole

In chloroform, 0.78 g of the naloxyindole hydrochloride obtained in Example 1 was suspended and saturated aqueous solution of sodium bicarbonate was added to the suspension, followed by stirring of the resulting mixture at room temperature for one hour. The resulting mixture was extracted with chloroform three times. The combined organic layers were washed with saturated aqueous sodium chloride solution, dried and concentrated to give 0.6 g of pure naloxindole.

The analytical results of the obtained compound were as follows:

IR (KBr)cm$^1$: 3392, 2934, 2840, 1638, 1620, 1504, 1458, 928

NMR (CDCl$_3$): 1.78 (1H, d, j=12.7 Hz), 2.20–2.45 (2H, complex pattern ), 2.62 (2H, d, j=15.6 Hz ), 2.75–2.90 (2H, complex), 3.10–3.25 (4H, complex), 5.15–5.30 (2H, m), 5.70 (1H, s), 5.90 (1H, m), 6.5 (1H, d, j=8.3 Hz), 6.57 (1H, d, j=8.3 Hz), 7.02 (1H, m), 7.14 (1H, m), 7.26 (1H, m), 7.40 (1H, d, j=7.8 Hz), 8.19 (1H, s) MASS (FAB): 399 (M+-1)

In the above-described operation, if 2-fluorohydrazine is used in place of phenylhydrazine, 7'-fluoronaloxindole is obtained. If 4-fluorohydrazine is used in place of phenylhydrazine, 5'-fluoronaloxindole is obtained. If 2-methylphenylhydrazine is used, 7'-methylnaloxindole is obtained. If 4-methylphenylhydrazine is used, 5'-methylnaloxindole is obtained. If 4-nitrophenylhydrazine is used, 5'-nitronaloxindole is obtained.

EXAMPLE 3

Synthesis of Naltrindole Methanesulfonic Acid Salt

In 20 ml of ethanol, 1 g of naltrexone hydrochloride and 0.3 ml of phenylhydrazine were dissolved and the resulting mixture was heated under reflux. To the mixture, 2.6 ml of methanesulfonic acid was added and the resulting mixture was heated under reflux for another 1.5 hours with stirring. The mixture was then cooled to room temperature and the precipitated crystals were filtered to afford 1.1 g of naltrindole methanesulfonic acid salt. The obtained salt was recrystallized from ethanol to give 0.93 g of naltrindole methanesulfonic acid salt (decomposition point: >300° C.).

After drying the thus obtained naltrindole methanesulfonic acid salt, the salt showed the following satisfactory elementary analytical results: Elementary Analysis: as $C_{26}H_{26}N_2O_3 \cdot H_2O \cdot CH_3SO_3H$

| | C | H | N | S |
|---|---|---|---|---|
| Calcd. | 61.35 | 6.10 | 5.30 | 6.07 |
| Found | 61.61 | 6.04 | 5.28 | 5.77 |

EXAMPLE 4

Synthesis of Naltrindole

In 10 ml of chloroform, 0.9g of the naltrindole methanesulfonic acid salt obtained in Example 3 was suspended and saturated aqueous solution of sodium bicarbonate was added to the suspension, followed by stirring at room temperature. The resulting mixture was extracted with chloroform three times. The combined organic layers were washed with saturated aqueous sodium chloride solution, dried and concentrated to give 0.7 g of pure naltrindole.

The analytical results of the obtained compound were as follows:

IR (KBr) cm$^{-1}$: 3392, 2926, 2838, 1638, 1622, 1504, 1458 NMR (CDCl$_3$): 0.07 (2H, m), 0.58 (2H, 0.88 (1H, m), 1.80 (1H, m), 2.20–2.60 (complex pattern ), 2.63 (1H, d, j=153 Hz), 2.90 (1H, d, j=15.3 Hz), 3.14 (1H, d, j=18.5 Hz), 5.70 (1H, s), 6.59 (2H, m), 7.03 (1H, m), 7.18 (1H, m), 7.29 (1H, d, j=8.3 Hz), 7.41 (1H, d, j=8.3 Hz)

MASS (FAB): 413(M-1), 415(M+1)

EXAMPLE 5

The antagonistic activities of the naloxindole hydrochloride and the naltrindole methanesulfonic acid salt obtained in Examples 1 and 3 were determined by the following method:

Guinea pig ileum (containing μ and κ receptors) and mouse vas deferens were taken out and the organs were subjected to electric stimulations. The activities of the compounds for inhibiting the suppression of contraction of the organs by three agonists, that is, morphine (μ), EKC (κ) and DADLE (δ) were measured.

The results are shown in Table 1.

TABLE 1

Antagonism Between NTI and NLI in vitro

| Antagonist | | Slope | γ | pA$_2$ (50% Confidence Limit) | Ke (nM) | μ/δ | κ/δ |
|---|---|---|---|---|---|---|---|
| NTI | μ | 1.330 | 0.791 | 7.42 (7.26–7.58) | 38.0 | 91 | 104 |
| | κ | 1.807 | 0.941 | 7.36 (7.30–7.43) | 43.7 | | |
| | δ | 1.354 | 0.863 | 9.38 (8.95–9.81) | 0.42 | | |
| NLI | μ | −0.063 | −0.062 | 6.86 ± 0.01* | 138 | 251 | 407 |
| | κ | 0.105 | 0.149 | 6.85 ± 0.08* | 141 | | |
| | δ | 1.066 | 0.936 | 9.26 (9.04–9.48) | 0.55 | | |

*mean ± S.E.

As can be seen from Table 1, comparing NTI and NLI, NLI is slightly inferior to NTI in the affinity to δ receptors. However, as for the selectivity to the δ receptors with respect to μ and κ receptors, NTI showed about 100 times for μ and κ receptors, while NLI showed about 250 times and about 400 times for μ and κ receptors, respectively, which are extremely high.

whether the concentrations of NLI and NTI give influence on the antagonistic effects for each receptor is shown in FIGS. 1 and 2.

As shown in FIGS. 1 and 2, the antagonistic activity of NTI increases proportionally with its concentration. On the other hand, as for NLI, the activity for δ receptor alone was concentration-dependent while the activities for μ and κ receptors did not show dependency on the concentration. This means that the higher the concentration of NLI, the higher the selectivity for δ receptors with respect to the selectivities to μ and κ receptors. Thus, NLI is an excellent and ideal δ-selective antagonist.

EXAMPLE 6

Suppression of Mitogen Reaction

If mouse spleen cells are cultured in vitro in the presence of concanavalin A (hereinafter referred to as "ConA" for short), the cells are divided and proliferated (mitogen reaction). In this system, the immunosuppressive agent of the present invention or cyclosporin A as a comparative example was added to the culture medium and the effects to the mitogen reaction were examined.

More particularly, C57BL/6 mouse was sacrificed and the spleen was removed. The spleen cells were suspended in RPMI 1640 culture medium containing 10% fetal calf serum (hereinafter referred to as "RPMI 1640" for short) so as to prepare a spleen cell suspension ($5 \times 10^6$ cells/ml). In the wells of a flat-bottomed 96-well microplate, 100 μl of the suspension was placed and then 50 μl of RPMI 1640 containing ConA (4 μg/ml) as well as 50 μl of RPMI 1640 containing the test compound in the concentration shown in Table 2 were added. The cells were cultured for 48 hours (37° C. 5%$CO_2$) As a control, 50 μl of RPMI 1640 was added. Eight hours before the termination of the culture, 2 μ Ci of [$^3$H] thymidine was termination of the culture, added. After termination of the culture, the cells were collected on a filter paper by using a cell harvester. After drying the filter paper, the filter paper was placed in a vial containing toluene-based scintillator and the radioactivity was measured by a liquid scintillation counter.

The suppression rate of mitogen reaction was calculated according to the following equation:

Suppresion Rate of Mitogen Reaction (%) =

$$\frac{\text{(Radioactivity of Control Group (cpm))} - \text{(Radioactivity of Test Group (cpm))}}{\text{(Radioactivity of Control Group (cpm))} - \text{(Radioactivity When Not Containing ConA and Test Compound (cpm))}} \times 100$$

The results are shown in Table 2.

TABLE 2

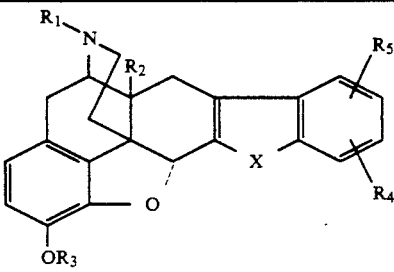

| Test Compound | | | | | | Number | Concentration | Suppression Rate |
|---|---|---|---|---|---|---|---|---|
| $R_1$ | $R_2$ | $R_3$ | X | $R_4$ | $R_5$ | of Cases | (μg/ml) | of Mitogen Reaction (%) |
| cyclopropylmethyl | OH | H | NH | H | H (NTI) | 3 | 50 | 100 |
| | | | | | | | 10 | 77 |
| | | | | | | | 1 | 12 |
| cyclopropylmethyl | OH | H | NH | 5'-Me | H | 3 | 50 | 100 |
| | | | | | | | 10 | 34 |
| | | | | | | | 1 | 8 |
| cyclopropylmethyl | OH | H | NH | 5'-Cl | H | 3 | 50 | 100 |
| | | | | | | | 10 | 37 |
| | | | | | | | 1 | 12 |
| cyclopropylmethyl | OH | H | NH | 5'-Br | H | 3 | 50 | 100 |
| | | | | | | | 10 | 40 |
| | | | | | | | 1 | 7 |
| cyclopropylmethyl | OH | H | NH | 6'-Me | H | 3 | 50 | 100 |
| | | | | | | | 10 | 28 |
| | | | | | | | 1 | 0 |
| cyclopropylmethyl | OH | H | NH | 7'-F | H | 3 | 50 | 100 |
| | | | | | | | 10 | 61 |
| | | | | | | | 1 | 15 |
| cyclopropylmethyl | OH | H | NH | 7'-Cl | H | 3 | 50 | 100 |
| | | | | | | | 10 | 75 |
| | | | | | | | 1 | 15 |
| cyclopropylmethyl | OH | H | NH | 7'-$NO_2$ | H | 3 | 50 | 100 |
| | | | | | | | 10 | 55 |
| | | | | | | | 1 | 5 |
| cyclopropylmethyl | OH | H | NH | 4',5'-benzo | | 3 | 50 | 88 |
| | | | | | | | 10 | 30 |
| | | | | | | | 1 | 2 |
| cyclopropylmethyl | OH | Me | NH | H | H | 3 | 50 | 100 |
| | | | | | | | 10 | 65 |
| | | | | | | | 1 | 9 |
| cyclopropylmethyl | OAc | H | NH | H | H | 3 | 50 | 100 |
| | | | | | | | 10 | 70 |
| | | | | | | | 1 | 2 |
| cyclopropylmethyl | OAc | Ac | NH | H | H | 3 | 50 | 100 |
| | | | | | | | 10 | 55 |
| | | | | | | | 1 | 4 |
| cyclopropylmethyl | OH | H | O | H | H (NTB) | 3 | 50 | 100 |
| | | | | | | | 10 | 41 |
| | | | | | | | 1 | 14 |
| cyclopropylmethyl | OH | H | NMe | H | H | 3 | 50 | 100 |
| | | | | | | | 10 | 69 |
| | | | | | | | 1 | 15 |
| allyl | OH | H | NH | H | H (NLI) | 3 | 50 | 100 |

TABLE 2-continued

| R1 | R2 | R3 | M | R4 | R5 | Number of Cases | Concentration (μg/ml) | Suppression Rate of Mitogen Reaction (%) |
|---|---|---|---|---|---|---|---|---|
|  |  |  |  |  |  |  | 10 | 56 |
|  |  |  |  |  |  |  | 1 | 12 |
| allyl | OH | H | O | H | H | 3 | 50 | 100 |
|  |  |  |  |  |  |  | 10 | 45 |
|  |  |  |  |  |  |  | 1 | 6 |
| allyl | OH | H | NMe | H | H | 3 | 50 | 100 |
|  |  |  |  |  |  |  | 10 | 50 |
|  |  |  |  |  |  |  | 1 | 13 |
| allyl | OH | Me | NH | H | H | 3 | 50 | 100 |
|  |  |  |  |  |  |  | 10 | 32 |
|  |  |  |  |  |  |  | 1 | 17 |
| allyl | OAc | Ac | NH | H | H | 3 | 50 | 100 |
|  |  |  |  |  |  |  | 10 | 40 |
|  |  |  |  |  |  |  | 1 | 2 |
| allyl | OH | H | NH | 5'-Me | H | 3 | 50 | 100 |
|  |  |  |  |  |  |  | 10 | 45 |
|  |  |  |  |  |  |  | 1 | 22 |
| allyl | OH | H | NH | 7'-Cl | H | 3 | 50 | 100 |
|  |  |  |  |  |  |  | 10 | 50 |
|  |  |  |  |  |  |  | 1 | 17 |
| Me | H | H | NH | H | H | 3 | 50 | 52 |
|  |  |  |  |  |  |  | 10 | 12 |
|  |  |  |  |  |  |  | 1 | 0 |
| CsA |  |  |  |  |  | 3 | 1 | 100 |
|  |  |  |  |  |  |  | 0.1 | 98 |
|  |  |  |  |  |  |  | 0.01 | 65 |

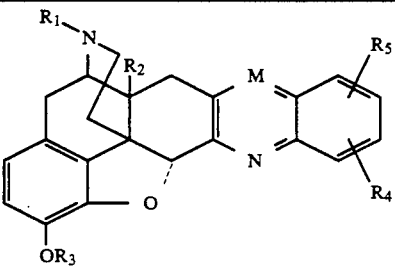

| Test Compound | | | | | | Number | Concentration | Suppression Rate |
| R1 | R2 | R3 | M | R4 | R5 | of Cases | (μg/ml) | of Mitogen Reaction (%) |
|---|---|---|---|---|---|---|---|---|
| cyclopropylmethyl | OH | H | CH | H | H | 3 | 50 | 75 |
|  |  |  |  |  |  |  | 10 | 43 |
|  |  |  |  |  |  |  | 1 | 15 |
| cyclopropylmethyl | OH | H | N | H | H | 3 | 50 | 55 |
|  |  |  |  |  |  |  | 10 | 34 |
|  |  |  |  |  |  |  | 1 | 10 |
| CsA |  |  |  |  |  | 3 | 1 | 100 |
|  |  |  |  |  |  |  | 0.1 | 98 |
|  |  |  |  |  |  |  | 0.01 | 65 |

As shown in Table 2, it was confirmed that the immunosuppressive agent of the present invention suppresses the proliferation of the cells induced by ConA.

Further, in the in vitro test employing ConA stimulation, cyclosporin A exhibited cytotoxicity in the concentration of lg/ml while the immunosuppressive agent of the present invention did not show any toxicity in the same concentration. Thus, it was confirmed that the immunosuppressive agent of the present invention exhibits an activity comparable to that of cyclosporin A while its toxicity is lower, so that the immunosuppressive agent of the present invention has ideal characteristics as an immunosuppressive agent.

EXAMPLE 7

Suppression of MLR Reaction

If spleen cells from two different lines of mouse which are genetically different, the spleen cells recognize the other type of cells, and the cells are divided and proliferated (MLR reaction).

In this system, hydrochloric acid salt of NTI, NTB or NLI, or for comparison, cyclosporine A was added to the reaction medium and their effect to the MLR reaction was examined.

Balb/c mouse was sacrificed and the spleen was removed. The spleen cells were suspended in RPMI 1640 to prepare a spleen cell suspension ($1 \times 10^7$ cells/ml). The spleen cells were then cultured in mitomycin C-containing RPMI 1640 for 30 minutes (37° C.) so as to carry out the mitomycin treatment. On the other hand, C57BL/6 mouse was sacrificed and spleen cell suspension ($1 \times 10^6$ cells/ml) was prepared using RPMI 1640.

In the wells of a 96-well flat-bottomed microplate, 100 μl of C57BL/6 mouse spleen cell suspension, 50 μl of mitomycin-treated Balb/c mouse spleen cell suspension and 50 μl of RPMI 1640 containing the test compound were placed and the cells were cultured for 72 hours (37° C., 5%CO$_2$). As a control, 50 μl of RPMI 1640 was added. Eight hours before the termination of the culture, 2 μCi of [$^3$H] thymidine was added. After termination of the culture, the cells were collected on a filter paper by using a cell harvester. After drying the filter paper, the filter paper was placed in a vial containing toluene-based scintillator and the radioactivity was measured by a liquid scintillation counter.

The suppression rate of MLR reaction was calculated according to the following equation:

Suppression Rate of MLR Reaction (%) =

$$\frac{(\text{Radioactivity of Control Group (cpm)}) - (\text{Radioactivity of Test Group (cpm)})}{(\text{Radioactivity of Control Group (cpm)}) - (\text{Total Radioactivities of Spleen Cells Alone of Both Lines (cpm)})} \times 100$$

The results are shown in Table 3.

TABLE 3

| Test Compound | Number of Cases | Concentration (μg/ml) | Suppression Rate of MLR Reaction (%) |
|---|---|---|---|
| NTI | 3 | 50 | 100 |
|  |  | 10 | 100 |
|  |  | 1 | 0 |
| NTB | 3 | 50 | 100 |
|  |  | 10 | 81 |
|  |  | 1 | 5 |
| NLI | 3 | 50 | 100 |
|  |  | 10 | 95 |
|  |  | 1 | 22 |
| CsA | 3 | 10 | 100 |
|  |  | 1 | 100 |
|  |  | 0.1 | 100 |

As shown in Table 3, it was confirmed that MLR reaction is suppressed by hydrochloric acid salts of NTI, NTB and NLI.

EXAMPLE 8

Suppression of Graft versus Host Reaction

It is known that a graft versus host reaction occurs when spleen cells of a parent are transplanted to F1 mouse. In this system, NTI, NTB or cyclosporine A was administered to F1 mouse and the effects of these compounds on the graft versus host reaction were examined.

C57BL/6 mouse was sacrificed and the spleen was removed. Using phosphate buffered saline, a suspension of spleen cells ($2 \times 10^8$ cells/ml) was prepared. To plantar of left hind leg of BDF1 mice, 50 μl of this spleen cell suspension was subcutaneously injected. From the day of this injection, each test compound was administered once a day for 5 days. The dose was 100 mg/kg and suspensions of the test compounds in 0.5% carboxymethyl cellulose (hereinafter referred to as "CMC") were orally administered. To the control group, 0.5% CMC alone was administered in the same manner. On the 7th day from the day of injection of the spleen cells, the mice were sacrificed and popliteal lymph nodes of right and left hind legs were removed and the weight of the lymph nodes was measured. The difference between the weight of the lymph nodes of the right and left hind legs was calculated and the difference was used as an index of the graft versus host reaction. The obtained results were analyzed by Student's t-test. The results which are significant as compared with the control group and the level of significance are less than 0.02 or 0.05 are marked "**" or "*", respectively.

The suppression rate of graft versus host reaction was calculated according to the following equation:

Suppression Rate of Graft versus Host Reaction =

$$\frac{\substack{\text{Weight Difference between} \\ \text{Right and Left Lymph Nodes} \\ \text{in Control Group}} - \substack{\text{Weight Difference between} \\ \text{Right and Left Lymph} \\ \text{Nodes in Test Group}}}{\text{Weight Difference between Right and Left Lymph Nodes in Control Group}} \times 100$$

The results are shown in Table 4.

TABLE 4

| Test Compound | Number of Cases | Dose (mg/kg) | Suppression Rate of Graft versus Host Reaction (%) |
|---|---|---|---|
| NTI | 4 | 100 | 47* |
| NTB | 4 | 100 | 44** |
| CsA | 4 | 100 | 28 |

As shown in Table 4, the graft versus host reaction was suppressed by NTI and NTB. In this example, the administration of the test compounds was carried out orally and the activities were higher than that of cyclosporin A. This experimental model of graft versus host reaction is a famous experimental model of organ transplantation and the fact that the test compounds exhibited higher activities than that of cyclosporin A indicates that these compounds can be used as immunosuppressive agents.

INDUSTRIAL APPLICABILITY

The immunosuppressive agent of the present invention has largely improved toxicity when compared to the conventional cyclosporin A or FK-506 for which the toxicity is a drawback, and yet exhibits excellent immunosuppressive effect. Further, the immunosuppressive agent of the present invention can be administered orally. Thus, the immunosuppressive agent of the present invention may be used for suppressing the rejection of transplants in organ transplantations.

According to the process of producing the immunosuppressive agent of the present invention, the immunosuppressive agent may be produced by simple operations in a high yield, so that production of the immunosuppressive agent in industrial scale can be accomplished.

We claim:

1. A method for effecting immunosuppression in a subject, which comprises administering to a subject in need of immunosuppression, an amount of a δ-opioid receptor antagonist, or a pharmaceutically acceptable salt thereof, in an amount sufficient to effect immunosuppression in said subject chlorine, bromine, amino, nitro, $C_1$-$C_5$ alkyl, $C_1$-$C_5$ alkoxy or $R_4$ and $R_5$ together represent benzo.

wherein said δ-opioid antagonist is a compound represented by the formula (1):

[1]

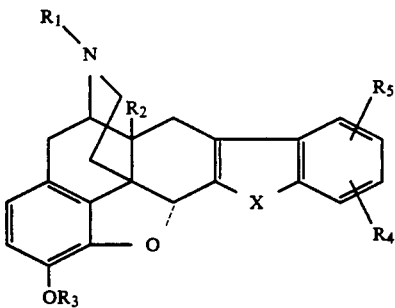

wherein $R_1$ represents $C_1$–$C_5$ alkyl, $C_3$–$C_6$ cycloalkylalkyl, $C_5$–$C_7$ cycloalkenylalkyl, aryl, aralkyl, $C_4$–$C_5$ trans-alkenyl, allyl or furan-2-ylalkyl, $R_2$ represents hydrogen, hydroxy or $C_1$–$C_5$ alkanoyloxy, $R_3$ represents hydrogen, $C_1$–$C_5$ alkyl or $C_1$–$C_5$ alkanoyl, X represents oxygen, sulfur or nitrogen to which a radical Y is attached, wherein Y represents hydrogen or $C_1$–$C_5$ alkyl, $R_4$ and $R_5$ individually represent hydrogen, fluorine, 2. The method of claim 1, wherein said δ-opioid antagonist is administered at a dose ranging from 1 mg to 10 g per day.

3. The method of claim 1, wherein said δ-opioid antagonist is administered orally.

4. The method of claim 1, wherein said δ-opioid antagonist is administered by peripheral injection.

5. The method of claim 1, wherein said δ-opioid antagonist is administered orally.

6. The method of claim 5, wherein said δ-opioid antagonist is administered at a dose ranging from 10 mg to 10 g per day.

7. The method of claim 1, wherein said subject is in need of suppression of a mixed lymphocyte reaction.

8. The method of claim 1, wherein said subject presents symptoms of graft versus host disease or requires immunosuppression due to rejection of a transplant.

9. The method of claim 1, wherein said subject is in need of suppression of a mixed lymphocyte reaction.

10. The method of claim 1, wherein said subject presents symptoms of graft versus host disease or requires immunosuppression due to rejection of a transplant.

* * * * *

UNITED STATES PATENT AND TRADEMARK OFFICE
CERTIFICATE OF CORRECTION

PATENT NO. : 5,332,818

DATED : July 26, 1994

INVENTOR(S) : Nagase et al.

It is certified that error appears in the above-identified patent and that said Letters Patent is hereby corrected as shown below:

Col. 14, line 63, delete "chlorine, bromine, amino,";

Col. 14, line 64, delete in its entirety;

Col. 14, line 65, delete in its entirety; and

Col. 15, line 24-25, after "fluorine," insert --chlorine, bromine, amino, nitro, $C_1$-$C_5$ alkyl, $C_1$-$C_5$ alkoxy or $R_4$ and $R_5$ together represent benzo.";

Signed and Sealed this

Twenty-third Day of May, 1995

*Attest:*

*Attesting Officer*

BRUCE LEHMAN

*Commissioner of Patents and Trademarks*